United States Patent [19]
Cook et al.

[11] Patent Number: 4,801,698
[45] Date of Patent: Jan. 31, 1989

[54] PROCESS FOR PREPARING DIAMINOPYRIMIDO(4,5-D)PYRIMIDINE GLYCOSIDE AND GLYCOTIDE

[75] Inventors: Phillip D. Cook; David A. Berry, both of Ann Arbor, Mich.

[73] Assignee: Warner-Lambert Company, Morris Plains, N.J.

[21] Appl. No.: 896,778

[22] Filed: Aug. 15, 1986

[51] Int. Cl.$^4$ ............................................. C07H 17/02
[52] U.S. Cl. ........................................ 536/28; 536/24; 536/29
[58] Field of Search ................. 536/24, 28, 29; 517/43

[56] References Cited
U.S. PATENT DOCUMENTS 4,352,795 10/1982 Cook ...................................... 536/28
4,531,001 7/1985 Robins et al. .......................... 536/28

OTHER PUBLICATIONS

Abst. 33, 85th Ann. Mtg., Am. Soc. Microb., Mar. 3-7, 1985.
Berman et al., Tet. Letters, 33:3099-3101 (1973).
Ishido et al., Bull. Chem. Soc. (Japan), 40:1007 (1967).

Primary Examiner—Johnnie R. Brown
Assistant Examiner—Elli Peselev
Attorney, Agent, or Firm—Ronald A. Daignault

[57] ABSTRACT

The aminoglycoside and aminoglycotide $N^4$-(2,3,5-tri-O-acetyl-$\beta$-D-ribofuranosyl)pyrimido[4,5-d]pyrimidine-4,8-diamine and $N^4$-(5-O-phosphono-$\beta$-D-ribofuranosyl-pyrimido[4,5-d]pyrimidine-4,8-diamine exhibit antiviral activity as well as cytotoxic activity against the L1210 and mammary 16/C tumor cell lines.

An improved method for their production involves the production of a sylilated intermediate and reaction of the intermediate with tetra-O-acetyl-$\beta$-D-ribofuranose in the presence of the specific catalyst trimethylsilyltrifluoromethanesulfonate.

2 Claims, No Drawings

PROCESS FOR PREPARING DIAMINOPYRIMIDO(4,5-D)PYRIMIDINE GLYCOSIDE AND GLYCOTIDE

BACKGROUND OF THE INVENTION

This invention relates to diaminopyrimido-pyrimidine glycosides and glycotides and to methods for their synthesis. More particularly, this invention concerns the novel compounds, $N^4$-(2,3,5-tri-O-acetyl-$\beta$-D-ribofuranosyl)pyrimido[4,5-d]pyrimidine-4,8-diamine and $N^4$-(5-O-phosphono-$\beta$-D-ribofuranosyl)pyrimido[4,5-d]pyrimidine-4,8-diamine, and an improved method or their production.

The aminoglycoside $N^4$-($\beta$-D-ribofuranosyl)pyrimido[4,5-d]pyrimidine-4,8-diamine was produced initially as an "equimolar ammonia adduct" of ammonia and 6-cyano-D-ribofuranosylpurine by Ishido et al., *Bull. Chem. Soc.* (Japan), 40: 1007 (1967).

Berman et al., *Tetrahedron Letters*, No. 33, 3099-3101 (1973) investigated this reaction further and demonstrated that the "ammonia adduct" of Ishido et al. was $N^4$-($\beta$-D-ribofuranosyl)pyrimido[4,5-d]pyrimidine-4,8-diamine. The reaction sequence employed by Ishido et al. and Berman et al. for the production of this aminoglycoside involved the catalyzed high temperature reaction of 6-cyanopurine with tetra-O-acetyl-$\beta$-D-ribose, followed by reaction with ammonia. The overall yield from this reaction, however is disappointing since yields from the first step are often of the order of 20%.

Burns, III, et al. demonstrated that the compound has broad spectrum antiviral activity, N. J. Burns, III et al., "Evaluation of a Novel Pyrimidopyrimidine Antiviral Agent," Paper No. A33, *Abstracts of the 85th Annual Meeting*, American Society for Microbiology, March, 1985. However, the compound is quite insoluble and its use as a pharmaceutical agent is thus impaired because of the attendant difficulties in delivering the compound in effective quantities to an organism.

SUMMARY OF THE INVENTION

There is provided, in accordance with the present invention, the novel antiviral compounds $N^4$-(2,3,5-tri-O-acetyl-$\beta$-D-ribofuranosyl)pyrimido[4,5-d]pyrimidine-4,8-diamine and $N^4$-(5-O-phosphono-$\beta$-D-ribofuranosyl)pyrimido[4,5-d]pyrimidine-4,8-diamine, and an improved method which produces the compounds in the desired $\beta$-anomeric form in higher overall yield from commonly available starting materials.

The method of this invention comprises the steps of a) reacting 6-cyanopurine with bis(trimethylsilyl)trifluoroacetamide in acetonitrile under reflux and thereafter with tetra-O-acetyl-$\beta$-D-ribofuranose in the presence of trimethylsilyltrifluoromethanesulfonate to stereospecifically produce 9-(tri-O-acetyl-$\beta$-D-ribofuranosyl)-6-cyanopurine in high yield; b) reacting said 9-(tri-O-acetyl-$\beta$-D-ribofuranosyl)-6-cyanopurine with methanolic ammonia in a sealed pressure vessel at ambient temperature to produce $N^4$-($\beta$-D-ribofuranosyl)pyrimido[4,5-d]pyrimidine-4,8-diamine; c) reacting said $N^4$-($\beta$-D-ribofuranosyl)pyrimido[4,5-d]pyrimidine-4,8-diamine with phosphoryl chloride in trimethylphosphate at a temperature below about 10° C. to produce $N^4$-5-O-phosphono-$\beta$-D-ribofuranosyl)pyrimidine-4,8-diamine or, alternatively reacting said $N^4$-($\beta$-D-ribofuranosyl)pyrimido[4,5-d]pyrimidine-4,8-diamine with acetic anhydride in the presence of an acid scavenger to produce $N^4$-(2,3,5-tri-O-acetyl-$\beta$-D-ribofuranoxyl)pyrimido[4,5-d]pyrimidine-4,8-diamine.

DETAILED DESCRIPTION

The process of this invention departs from prior art methods of making $N^4$-($\beta$-D-ribofuranosyl)pyrimido[4,5-d]pyrimidine-4,8-diamine by first converting the starting material, 6-cyanopurine, to a sylilated intermediate, and reacting this intermediate with tetra-O-acetyl-$\beta$-D-ribofuranose in the presence of the specific catalyst, trimethylsilyltrifluromethanesulfonate, to produce 9-(2,3,5-tri-O-acetyl-$\beta$-D-ribofuranosyl)-6-cyanopurine.

The reaction to produce the silylated intermediate is carried out by reacting 6-cyanopurine with bis(trimethylsilyl)trifluoroacetamide in an inert polar organic solvent such as acetonitrile under reflux for a period of about one to two hours. The solvent is removed under vacuum, and the silylated intermediate which is thus formed may be used in the subsequent step without further purification.

The silylated intermediate is dissolved in an aprotic organic solvent such as methylene chloride and reacted with tetra-O-acetyl-$\beta$-D-ribofuranose at room temperature for a period sufficient to effect complete replacement of the silyl group by the acetylated ribofuranose. This is usually accomplished in less than two hours, generally in about one hour. This reaction step is carried out in the presence of greater than one molar equivalent of the specific catalyst trimethylsilyltrifluoromethanesulfonate, preferably 1.0 to 1.5 molar equivalents. This reaction affords the intermediate 9-(tri-O-acetyl-$\beta$-D-ribofuranosyl)-6-cyanopurine as a stable product in 98% yield. The prior art method, which involves a high temperature fusion of 6-cyanopurine with tetra-O-acetyl-$\beta$-D-ribofuranose (cf. Y. Isido et al., *Nippon Kagaku Zasshi*, 87: 752 (966)) produces the desired product in only about 23% yield.

In the next step of the process of this invention, the 9-(tri-O-acetyl-$\beta$-D-ribofuranosyl)-6-cyanopurine is reacted with methanolic ammonia in a pressure vessel to produce $N^4$-$\beta$-D-ribofuranosylpyrimido[4,5-d]pyrimidine-4,8-diamine. The vessel is charged with a methanolic solution of the substituted 6-cyanopurine together with a methanolic solution of ammonia, previously saturated at about 0° C., and sealed. The materials are stirred and allowed to react, with the temperature being allowed to rise to ambient during the reaction. This step of the process generally produces yields of the order of 75%. Thus, the process of the present invention produces desired anomerically pure $N^4$-$\beta$-D-ribofuranosylpyrimido[4,5-d]pyrimidine-4,8-diamine from the starting 6-cyanopurine in two steps in overall yields generally in excess of 70%.

The $N^4$-$\beta$-D-ribofuranosylpyrimido[4,5-d]pyrimidine-4,8-diamine is converted, if desired, to $N^4$-(2,3,5-tri-O-acetyl-$\beta$-D-ribofuranos-yl)pyrimido[4,5-d]pyrimidine-4,8-diamine in the next step of the process of this invention by the action of a pyridine solution of an acetylating agent such as acetic anhydride, in the presence of an acid scavenger such as 4-dimethylaminopyridine. This step may be carried out at ambient temperature, generally over a period of from 12 to 36 hours, preferably about 24 hours.

Alternatively, the $N^4$-$\beta$-D-ribofuranosylpyrimido[4,5-d]pyrimidine-4,8-diamine is converted, by the action of phosphoryl chloride in trimethylphosphate solution to $N^4$-(5-phosphono-$\beta$-D-ribofuranosyl)-pyrimido[4,5-d]pyrimidine-4,8-diamine. This reaction is carried out at a temperature of below about 10° C., preferably about 5° C., for a period of from one to five hours, preferably about three hours.

In a typical work-up, the crude reaction mixture is treated with aqueous sodium bicarbonate solution, which results ultimately in the production of the disodium salt of the glycotide. Desalting and purification of the disodium salt is accomplished by passing the crude product through a silica gel column and eluting with a 4:1 mixture of acetonitrile/water. This procedure is more effective than the method generally used for desalting glycotide salts which employs a charcoal column. The charcoal column method typically results in a loss of 25–50% of the material and rapid acid-catalyzed anomerization of the product to a equimolar mixture of the desired $\beta$-anomer and the undesirable $\alpha$-anomer caused by the acidic eluents employed. The $\alpha$-anomer is devoid of pharmacological activity. In contrast, the silica gel column method of the present invention results in very little loss of material, and the purified product is almost exclusively the desired pharmacologically active $\beta$-anomer.

The free acid form of $N^4$-(5-O-phosphonyl-$\beta$-D-ribofuranosyl)pyrimido[4,5-d]pyrimidine-4,8-diamine may be produced by passing an aqueous solution of the salt through an ion exchange resin such as Dowex 50 in the hydrogen ion form. The free acid may then be converted to the desired salt form by reaction with one equivalent of a base to produce the mono-salt or two equivalents to produce the di-salt.

The compounds of the present invention form pharmaceutically accepable salts with organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl) aminomethane; and the like. (See for example, "Pharmaceutical Salts," *J. Pharm. Sci.* 66 (1): 1–19 (1977)).

The salts are prepared by contacting the free acid form of the compounds of this invention with a sufficient amount of the desired base to produce the salt in the conventional manner. The free acid forms may be regenerated, if desired, by treating the salt form with an ion exchange resin in the acid form.

The free acid forms of the compounds of this invention differ somewhat from their respective salt forms in such physical properties as melting point and solubility in polar solvents, but the salts are otherwise equivalent to their respective free acid forms for the purposes of the invention.

The $N^4$-(5-phosphono-$\beta$-D-robofuranosyl)-pyrimido[4,5-d]pyrimidine-4,8-diamine compound of the present invention possesses broad spectrum antiviral activity against a number of viruses including the herpes simplex virus types 1 and 2, coxsackie viruses B1 and B4, measles virus, parainfluenza virus type 3, vaccinia virus, and rhinovirus type 3.

In addition, the compound has demonstrated cytotoxic in vitro and in vivo activity against the murine L1210 leukemia cell line, and in vivo activity against the mammary 16/C tumor cell line. For example, in vitro tests, $N^4$-(5-phosphono-$\beta$-D-ribofuranosyl)-pyrimido[4,5-d]pyrimidine-4,8-diamine exhibited an IC$_{50}$ value of $1\times10^{-7}$ molar. In in vivo tests, % T/C values (mean survival times expressed as a percentage of control for standard laboratory animals inoculated with the transplanted tumor cell line) were 152 at a dose of 12.5 mg/kg, 197 at 25 mg/kg, 185 at 50 mg/kg, and 164 at 100 mg/kg. The protocol for the L1210 murine leukemia screening test is detailed in R. I. Geran et al., "Protocols for Screening Chemical Agents and Natural Products Against Animal Tumors and Other Biological Systems," *Cancer Chemotherapy Reports*, 3: 1–85 (1972). This test is considered highly predictive of efficacy in humans (cf. J. M. Venditti, "Relevance of Transplantable Animal-Tumor Systems to the Selection of New Agents for Clinical Trial," in *Pharmacological Basis of Cancer Chemotherapy*, Williams and Wilkins Co., Baltimore, pp. 245–270, 1975.)

In in vivo tests against the transplanted mammary 16/C tumor cell line, $N^4$-(5-phosphono-$\beta$-D-ribofuranosyl)pyrimido[4,5-d]pyrimidine-4,8-diamine exhibited % T/C values of 150 at a dose of 1.56 mg/kg, 158 at 3.12 6.25, and 25 mg/kg, and 162 at 50 mg/kg.

In in vivo tests of anti-tumor agents against transplanted tumor cell lines in standard laboratory animals, % T/C values greater than 125 are considered indicative of significant activity.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butte,, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation in is unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as antiviral agents, the compounds utilized in the pharmaceutical method of this invention are administered to the patient at dosage levels of from 125 to 500 mg per day. The specific dosages employed, however, may be varied depending upon the requirements of the patient, the severity of the condition being treated, and the activity of the compound being employed. The determination of optimum dosages for a particular situation is within the skill of the art.

The following preparative examples are provided to enable one skilled in the art to practice the invention, and are illustrative thereof. They are not to be read as limiting the scope of the invention as it is defined by the appended claims.

EXAMPLE

Step A—Preparation of 6-cyanopurine

A mixture of 1188 g (4.66 mol) of 6-iodopurine and 644 g (7.19 mol) of copper (I) cyanide in 12 liters of pyridine was heated under reflux with vigorous stirring in a nitrogen atmosphere. After two and one-half hours, the solution was cooled to about −70° C. and the pyridine was removed under vacuum to leave a dark solid which was pulverized in a blender.

This material was extracted with diethyl ether in a Soxhlet extractor. The solid which precipitated from the ether extract was collected by filtration and redissolved in 4 liters of methanol. The methanol-insoluble solids were removed by filtration and the filtrate was clarified with charcoal. The clear filtrate was concentrated in vacuo (12 torr, 40° C.) to yield 536 g (88%) of 6-cyanopurine, mp 183°–185° C.

Step B—Preparation of 9-tri-O-acetyl-β-D-ribofuranosyl)-6-cyanopurine

A mixture of 100 g (0.69 mol) of 6-cyanopurine and 349 g (1.35 mol) of bis(trimethylsilyl)trifluoroacetamide in 1 liter of acetonitrile was heated under reclux in a nitrogen atmosphere for one and one-half hours.

After this time, the mixture was concentrated under vacuum (initially at 10 torr, then subsequently at 1 torr and 60° C.) to yield the crude silylated intermediate. This material was dissolved in 1 liter of dichloromethane and 219.5 g (0.69 mol) of tetra(O-acetyl-β-D-ribofuranose and 220 g (0.99 mol) of trimethylsilyltrifluoromethanesulfonate were added.

The mixture was stirred to insure complete mixing and then allowed to stand. After one hour, thin-layer chromatographic analysis of the reaction mixture showed that no starting silylated purine remained. The reaction mixture was then poured, with vigorous stirring, into 1.5 liters of saturated, ice-cold aqueous sodium bicarbonate solution.

The layers were separated and the aquesous layer was extracted four times with 500-ml portions of ethyl acetate. The ethyl acetate extracts were combined with the original dichloromethane solution and the resulting mixture dried over anhydrous magnesium sulfate. The dried solution was concentrated under vacuum (initially at 10 torr and 50° C. and subsequently at 1 torr and 50° C.) to yield 274 g (98%) of 9-tri-O-acetyl-β-D-ribofuranosyl)-6-cyanopurine as a syrup which was used without further purification.

Step C—Preparation of $N^4$-(β-D-ribofuranosyl)pyrimido[4,5-d]pyrimidine-4,8-diamine A solution of 274 g (.68 mol) of 9-tri-O-acetyl-β-D-ribofuranosyl)-6-cyanopurine in 300 ml of methanol was added to a steel pressure reactor containing a solution of 240 g of ammonia on 800 ml of methanol at 0° C. The vessel was sealed and the reaction mixture was stirred for eighteen hours. During this time the temperature of the reaction mixture rose from 0° C. to 18° C. The reactor vessel was then opened and the white solid which had formed was collected by filtration and washed successively with 400 ml of methanol and 600 ml of diethyl ether. The solid was dried on vacuo (1 torr, 75° C.) to yield 151 g (75%) of $N^4$-(β-D-ribofuranosyl)-pyrimido-[4,5-d]pyrimidine-4,8-diamine, mp 209°–213.5° C.

Step D—Preparation of $N^4$-2,3,5-tri-O-acetyl-β-D-ribofuranosyl)pyrimido[4,5-d]pyrimidine-4,8-diamine A mixture of 1.179 g (4 mmol) of (β-D-ribofuranosyl)pyrimido[4,5-d]pyrimidine-4,8-diamine, 50 ml of dry pyridine, 366 mg (3 mmol) of 4-dimethylaminopyridine, and 1.5 g (14 mmol) of acetic anhydride was stirred at room temperature for 24 hours.

The solvents were removed under vacuum and the residue was coevaporated twice with xylenes. The residue was distributed between water and ethyl acetate. The ethyl acetate layer was separated and dried with magnesium sulfate, filtered, and evaporated under vacuum. Recrystallization of the residue from ethanol provided 1.2 g (71%) of N⁴-2,3,5-tri-O-acetyl-β-D-ribofuranosyl)pyrimido[4,5-d]pyrimidine-4,8-diamine as white needles, mp 135°–137° C. after drying at 100° C. under high vacuum for two hours. The proton magnetic resonance spectrum of this material in hexadeuterodimethylsulfoxide solution indicated only the β-anomer present.

Step E—Preparation of N⁴-(β-D-ribofuranosyl)pyrimido[4,5-d]pyrimidine-4,8-diamine A solution of 2.0 g (4.76 mmol) of N⁴-2,3,5-tri-O-acetyl-β-D-ribofuranosyl)pyrimido[4,5-d]pyrimidine-4,8-diamine and 100 ml of methanolic ammonia (saturated at 5°–10° C.) was held at room temperature in a sealed stainless steel reaction vessel for twenty-four hours.

After this time, the white crystals which had formed were collected by filtration, washed with methanol, and dried at 100° C. under high vacuum for one hour to yield 1.3 g (95%) of N⁴-(β-D-ribofuranosyl)-pyrimido[4,5-d]pyrimidine-4,8-diamine. The proton magnetic resonance spectrum of this material in hexadeuterodimethylsulfoxide solution indicated only the β-anomer present.

Step F—Preparation of N⁴-(5-O-phosphono-β-D-ribofuranosyl)pyrimido[4,5-d]pyrimidine-4,8-diamine disodium salt A mixture of 5.91 g (20 mmol) of N⁴-(β-D-ribofuranosyl)pyrimido[4,5-d]pyrimidine-4,8-diamine and 120 ml of dry trimethylphosphate was cooled to 5° C. and rapidly stirred as 9.2 g (60 mmol) of phosphorus oxychloride was added dropwise over a period of one-half hour. During this addition, the temperature of the reaction mixture was held between 5° C. and 8° C. After addition was complete, the mixture was stirred at 5° C. for two and one-half hours.

The yellow solution which resulted was cooled to −20° C. and added dropwise with rapid stirring to 2.5 liters of diethyl ether which had been previously cooled to −40° C. Following the addition, the mixture was stirred for an additional one-quarter hour and the ether decanted. Two liters of ether, cooled to −20° C., was added to the syrupy residue and stirring continued for several minutes. This process was twice repeated.

While still cold, the syrupy residue was treated with a mixture of 125 g of crushed ice and 100 ml of cold saturated aqueous sodium bicarbonate solution. This mixture was held at 5° C. overnight and then extracted twice with 250-ml portions of diethyl ether. The light yellow solution was evaporated under vacuum (20 torr, 50° C.) to a final volume of 75 ml. This solution was treated with 150 ml of ethanol and the resulting syrupy precipitate was triturated three times with 150 ml of ethanol to effect crystallization.

The powdery material was dissolved in 150 ml of water, treated with 50 g of silica gel, and evaporated under reduced pressure. The residue was placed on a column of 250 g of silica gel (packed with 4:1 acetonitrile/water) and eluted with 4:1 acetonitrile/water to yield only one fraction which absorbed UV, charred with $H_2SO_4$, and was salt free. Evaporation of this fraction at 20 torr and 50° C. yielded 6.5 g of N⁴-(5-O-phosphono-β-D-ribofuranosyl)pyrimido[4,5-d]pyrimidine-4,8-diamine disodium salt as an off-white powder. The proton magnetic resonance spectrum of this material in hexadeuterodimethylsulfoxide solution indicated only the β-anomer present.

We claim:

1. A process for preparing N⁴-(5-phosphono-β-D-ribofuranosyl)pyrimido[4,5-d]pyrimidine-4,8-diamine or N⁴-(4 2,3,5-tri-O-acetyl-β-D-ribofuranosyl)-pyrimido[4,5-d]pyrimidine-4,8-diamine comprising the steps of
    (a) reacting 6-cyanopurine with bis(trimethylsilyl)trifluoroacetamide in acetonitrile under reflux and thereafter with tetra-O-acetyl-β-D-ribofuranose in the presence of trimethylsilyltrifluoromethanesulfonate catalyst to produce 9-(tri-O-acetyl-β-D-ribofuranosyl)-6-cyanopurine in high yield;
    (b) reacting said 9-(tri-O-acetyl-β-D-ribofuranosyl)-6-cyanopurine with ammonia in a sealed pressure vessel at a temperature below about 15° C. to produce N⁴-(β-D-ribofuranosyl)pyrimido[4,5-d]pyrimidine-4,8-diamine;
    (c) reacting said N⁴-(β-D-ribofuranosyl)-pyrimido[4,5-d]pyrimidine-4,8-diamine with acetic anhydride in the presence of an acid scavenger to produce N⁴-(2,3,5-tri-O-acetyl β-D-ribofuranosyl)-pyrimido[4,5-d]pyrimidine-4,8-diamine or, alternatively reacting said N⁴-(β-D-ribofuranosyl)-pyrimido[4,5-d]pyrimidine-4,8-diamine with phosphoryl chloride in trimethylphosphate at a temperature below about 10° C. to produce N⁴-(5-O-phosphono-β-D-ribofuranosyl)pyrimido[4,5-d]pyrimidine-4,8-diamine.

2. The process as defined by claim 1 wherein said catalyst is present in an amount of between about 1.0 to 1.5 molar equivalents relative to said 6-cyanopurine.

* * * * *